(12) United States Patent
Goffe

(10) Patent No.: US 7,396,530 B2
(45) Date of Patent: Jul. 8, 2008

(54) METHOD OF TREATING GRANULOMA ANNULARE OR SARCOID

(75) Inventor: Bernard S. Goffe, Seattle, WA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/149,031

(22) Filed: Jun. 8, 2005

(65) Prior Publication Data

US 2006/0013818 A1 Jan. 19, 2006

Related U.S. Application Data

(60) Provisional application No. 60/578,768, filed on Jun. 9, 2004, provisional application No. 60/579,096, filed on Jun. 10, 2004.

(51) Int. Cl.
A61K 39/395 (2006.01)

(52) U.S. Cl. .................................. 424/133.1; 424/144.1

(58) Field of Classification Search ........................ None
See application file for complete search history.

(56) References Cited

U.S. PATENT DOCUMENTS

| | | | |
|---|---|---|---|
| 5,002,869 A | 3/1991 | Schlossman et al. | |
| 5,071,964 A | 12/1991 | Dustin et al. | |
| 5,597,567 A | 1/1997 | Whitcup et al. | |
| 5,622,700 A | 4/1997 | Jardieu et al. | |
| 5,730,983 A | 3/1998 | Wegner et al. | |
| 5,932,448 A | 8/1999 | Tso et al. | |
| 5,997,867 A | 12/1999 | Waldmann et al. | |
| 6,037,454 A | 3/2000 | Jardieu et al. | |
| 6,818,638 B2 * | 11/2004 | Baenteli et al. | ............. 514/183 |

FOREIGN PATENT DOCUMENTS

| | | |
|---|---|---|
| CA | 2008368 | 6/1991 |
| EP | 0 346 078 A2 | 12/1989 |
| EP | 0 379 904 B1 | 5/1996 |
| EP | 0 387 668 B1 | 12/1996 |
| WO | WO 90/10652 | 9/1990 |
| WO | WO 90/13281 | 11/1990 |
| WO | WO 90/15076 | 12/1990 |
| WO | WO 91/16927 | 11/1991 |
| WO | WO 91/16928 | 11/1991 |
| WO | WO 91/18011 | 11/1991 |
| WO | WO 93/06864 | 4/1993 |
| WO | WO 93/21953 | 11/1993 |
| WO | WO 98/23761 | 6/1998 |
| WO | WO 98/51343 | 11/1998 |

OTHER PUBLICATIONS

Kreuter A et al Failure of etanercept therapy in disseminated granuloma annulare.Arch Dermatol. Sep. 2006;142(9):1236-7; author reply 1237.*

Buechner et al., "Identification of T-cell subpopulations in granuloma annulare" *Arch Dermatol.* 119 (2) :125-128 (Feb. 1983).

Campana et al., "Human leukocyte function-associated antigens on lympho-hemopoietic precursor cells" *European Journal of Immunology* 16 (5) :537-542 (May 1986).

Dabski et al., "Generalized granuloma annulare: clinical and laboratory findings in 100 patients" *J Am Acad Dermatol.* 20 (1) :39-47 (Jan. 1989).

Desroches et al., "Regulation and Functional Involvement of Distinct Determinants of Leucocyte Function-Associated Antigen 1 (LFA-1) in T-Cell Activation In Vitro" *Scand. J. Immunol.* 33 :277-286 (1991).

Fekete et al., "Involvement of Lymphocyte Function-Associated Antigen-1 (LFA-1) But Not ICAM-1 in a Radioactive Leukocyte Cell-Mediated Immunity (LA-CMI) Assay" *J. Clin. Lab. Immunol.* 31:145-149 (1990).

Friedman-Birnbaum, "Generalized and localized granuloma annulare" *Int J Dermatol.* 25(6) :364-366 (Jul. 1986).

Hildreth et al., "A Human Lymphocyte-associated Antigen Involved in Cell-mediated Lympholysis" *European Journal of Immunology* 13:202-208 (1983).

Kipnis et al., "Biologic treatments for psoriasis" *J Am Acad Dermatol.* 52(4):671-682 (Apr. 2005).

Modlin et al., "Immunopathologic demonstration of T lymphocyte subpopulations and interleukin 2 in granuloma annulare" *Pediatr Dermatol.* 2(1):26-32 (Jul. 1984).

Muhlbauer et al., "Granuloma annulare" *J Am Acad Dermatol.* 3(3):217-230 (Sep. 1980).

Nishimura et al., "The role of lymphokine-activated cell-associated antigen. III. Inhibition of T-cell activation by monoclonal killer-blocking antibody" *Cellular Immunology* 107(1):32-39 (Jun. 1987).

Sanchez-Madrid et al., "Mapping of antigenic and functional epitopes on the alpha- and beta-subunits of two related mouse glycoproteins involved in cell interactions, LFA-1 and Mac-1" *J Exp Med.* 158(2):586-602 (Aug. 1, 1983).

Smith et al., "Granuloma annulare" *Int J Dermatol.* 36(5):326-333 (May 1997).

Springer et al., "LFA-1 and Lyt-2, 3, molecules associated with T lymphocyte-mediated killing; and Mac-1, an LFA-1 homologue associated with complement receptor function" *Immunol. Rev.* 68:171-195 (1982).

Taylor et al., "The expression of CD18 is increased on Trisomy 21 (Down syndrome) lymphoblastoid cells" *Clinical & Experimental Immunology* 71(2):324-328 (Feb. 1988).

Werther et al., "Humanization of an Anti-Lymphocyte Function-Associated Antigen (LFA) -1 Monoclonal Antibody and Reengineering of the Humanized Antibody for Binding to Rhesus LFA-1" *J. of Immunology* 157:4986-4995 (1996).

* cited by examiner

*Primary Examiner*—Maher M. Haddad
(74) *Attorney, Agent, or Firm*—Lee K. Tan

(57) ABSTRACT

The invention provides a method of alleviating a granuloma annulare or a sarcoid disease by administering to a patient having the disease, a therapeutically effective amount of an LFA-1 antagonist.

20 Claims, 1 Drawing Sheet

```
                        SEQUENCE LISTING

<160> NUMBER OF SEQ ID NOS: 4

<210> SEQ ID NO 1
<211> LENGTH: 107
<212> TYPE: PRT
<213> ORGANISM: Artificial sequence
<220> FEATURE:
<223> OTHER INFORMATION: sequence is synthesized

<400> SEQUENCE: 1

Asp Ile Gln Met Thr Gln Ser Pro Ser Ser Leu Ser Ala Ser Val
  1               5                  10                  15

Gly Asp Arg Val Thr Ile Thr Cys Arg Ala Ser Lys Thr Ile Ser
                 20                  25                  30

Lys Tyr Leu Ala Trp Tyr Gln Gln Lys Pro Gly Lys Ala Pro Lys
                 35                  40                  45

Leu Leu Ile Tyr Ser Gly Ser Thr Leu Gln Ser Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

His Asn Glu Tyr Pro Leu Thr Phe Gly Gln Gly Thr Lys Val Glu
                 95                 100                 105

Ile Lys

<210> SEQ ID NO 2
<211> LENGTH: 121
<212> TYPE: PRT
<213> ORGANISM: Artificial sequence
<220> FEATURE:
<223> OTHER INFORMATION: sequence is synthesized

<400> SEQUENCE: 2

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Phe Thr
                 20                  25                  30

Gly His Trp Met Asn Trp Val Arg Gln Ala Pro Gly Lys Gly Leu
                 35                  40                  45

Glu Trp Val Gly Met Ile His Pro Ser Asp Ser Glu Thr Arg Tyr
                 50                  55                  60

Asn Gln Lys Phe Lys Asp Arg Phe Thr Ile Ser Val Asp Lys Ser
                 65                  70                  75

Lys Asn Thr Leu Tyr Leu Gln Met Asn Ser Leu Arg Ala Glu Asp
                 80                  85                  90
```

-continued

```
Thr Ala Val Tyr Tyr Cys Ala Arg Gly Ile Tyr Phe Tyr Gly Thr
                 95                 100                 105

Thr Tyr Phe Asp Tyr Trp Gly Gln Gly Thr Leu Val Thr Val Ser
            110                 115                 120

Ser

<210> SEQ ID NO 3
<211> LENGTH: 107
<212> TYPE: PRT
<213> ORGANISM: Mus musculus

<400> SEQUENCE: 3

Asp Val Gln Ile Thr Gln Ser Pro Ser Tyr Leu Ala Ala Ser Pro
  1               5                  10                  15

Gly Glu Thr Ile Ser Ile Asn Cys Arg Ala Ser Lys Thr Ile Ser
                 20                  25                  30

Lys Tyr Leu Ala Trp Tyr Gln Glu Lys Pro Gly Lys Thr Asn Lys
                 35                  40                  45

Leu Leu Ile Tyr Ser Gly Ser Thr Leu Gln Ser Gly Ile Pro Ser
                 50                  55                  60

Arg Phe Ser Gly Ser Gly Ser Gly Thr Asp Phe Thr Leu Thr Ile
                 65                  70                  75

Ser Ser Leu Glu Pro Glu Asp Phe Ala Met Tyr Tyr Cys Gln Gln
                 80                  85                  90

His Asn Glu Tyr Pro Leu Thr Phe Gly Thr Gly Thr Lys Leu Glu
                 95                 100                 105

Leu Lys

<210> SEQ ID NO 4
<211> LENGTH: 121
<212> TYPE: PRT
<213> ORGANISM: Mus musculus

<400> SEQUENCE: 4

Glu Val Gln Leu Gln Gln Pro Gly Ala Glu Leu Met Arg Pro Gly
  1               5                  10                  15

Ala Ser Val Lys Leu Ser Cys Lys Ala Ser Gly Tyr Ser Phe Thr
                 20                  25                  30

Gly His Trp Met Asn Trp Val Arg Gln Arg Pro Gly Gln Gly Leu
                 35                  40                  45

Glu Trp Ile Gly Met Ile His Pro Ser Asp Ser Glu Thr Arg Leu
                 50                  55                  60

Asn Gln Lys Phe Lys Asp Lys Ala Thr Leu Thr Val Asp Lys Ser
                 65                  70                  75

Ser Ser Ser Ala Tyr Met Gln Leu Ser Ser Pro Thr Ser Glu Asp
                 80                  85                  90

Ser Ala Val Tyr Tyr Cys Ala Arg Gly Ile Tyr Phe Tyr Gly Thr
                 95                 100                 105

Thr Tyr Phe Asp Tyr Trp Gly Gln Gly Thr Leu Val Thr Val Ser
            110                 115                 120

Ser
```

METHOD OF TREATING GRANULOMA ANNULARE OR SARCOID

This application claims the benefit of U.S. provisional application Ser. Nos. 60/578,768, filed on Jun. 9, 2004, and 60/579,096, filed on Jun. 10, 2004, which applications are incorporated herein by reference in their entirety.

FIELD OF THE INVENTION

The invention relates to treatment methods for granuloma annulare and sarcoid.

BACKGROUND OF THE INVENTION

Granuloma annulare encompasses an uncommon benign group of granulomatous diseases that include localized, disseminated (generalized), subcutaneous, and perforating types. Approximately 10% to 15% of patients have disseminated granuloma annulare (DGA, also referred to as GGA), which occurs primarily in adults and is characterized by multiple discrete or confluent papules with either an annular or nonannular configuration.[1-3] DGA occurs predominantly on the trunk and proximal extremities, and patients with DGA may present with hundreds of lesions. In approximately one third of cases, patients report symptoms of pruritus or burning sensations.[2] Histologically, DGA typically is characterized by areas of collagen alteration and elastic fiber degeneration in the middle and upper dermis surrounded by palisading inflammatory cells; the epidermis appears normal.[3-6] The inflammatory infiltrates in DGA are primarily composed of a mixture of histiocytes (macrophages) and lymphocytes.[4]

Although numerous theories have been proposed to explain the cause of granuloma annulare, the pathogenesis of this cutaneous disease remains unclear. Hypotheses include vasculitis, trauma-induced primary necrobiosis, monocytic release of lysosomal enzymes causing necrobiotic degeneration, and lymphocyte-mediated delayed hypersensitivity reaction (reviewed in Smith et al, 1997).[7] Several lines of evidence suggest a role for T-cell-mediated processes in the pathogenesis of granuloma annulare. Activated T lymphocytes, predominantly of the helper T (Th) cell phenotype, have been identified as the dominant lymphocyte in granuloma annulare infiltrates.[8-11] Activated Th cells secrete various proinflammatory cytokines, including interleukins, interferon-$\gamma$ (IFN-$\gamma$), and tumor necrosis factor-$\alpha$ (TNF-$\alpha$),[12] all of which have been detected in granuloma annulare lesions.[11,13] It has been suggested that initial infiltration of a minor, antigen-specific T-cell population (driven by the presence of unknown skin-specific antigens) is followed by recruitment of a large number of nonspecific T cells by means of nonspecific inflammatory cytokine and chemokine production.[14]

Granuloma annulare lesions typically persist for 3 to 4 years, and following spontaneous resolution of lesions, relapse may occur.[3] There is no standard treatment regimen or approach employed in the management of patients with granuloma annulare. Furthermore, the response to long-term conventional treatment is generally poor, and in many cases, the risk of serious toxicity does not outweigh the benefits of treatment.[2] However, as DGA can be cosmetically disfiguring and as the lesions can persist indefinitely[15], many different therapies have been tried with varied success, including cyclosporine,[16,17] isotretinoin,[18-20] etretinate,[21] topical and systemic corticosteroids,[22,23] fumaric acid esters,[24] psoralens plus ultraviolet A (PUVA),[25,26] potassium iodide,[27,28] pentoxifylline,[29] topical vitamin E,[30] hydroxychloroquine,[31] dapsone,[19,32,33] niacinamide,[34] low-dose chlorambucil,[35,36] clofazimine,[37] and a 5-lipoxygenase inhibitor plus vitamin E.[38] Many of these treatments are associated with potentially harmful side effects and require clinical and laboratory monitoring; due to their cumulative toxicity, many of these treatments cannot be administered chronically.

Thus, there is a need for a better method of treating granuloma annulare. The present invention satisfies this need and provides other benefits that will be apparent from the disclosure below.

SUMMARY OF THE INVENTION

The present invention provides a method of alleviating granuloma annulare conditions or sarcoid disease comprising administering to a patient having the disease, a therapeutically effective amount of an LFA-1 antagonist. The methods of the invention have the benefit of achieving rapid improvement and resolution of the disease and reduced side effects that are associated with conventional therapy for the disease. For example, conventional therapy with cyclosporine carries the risk of renal dysfunction and diarrhea may be a side effect with clofazimine treatment. The present method is effective to resolve the granuloma annulare within 2 months of initiation of therapy with the LFA-1 antagonist.

The granuloma annulare can be localized, disseminated (generalized; DGA), subcutaneous, or perforating type. In a specific embodiment, the granuloma annulare is disseminated granuloma annulare (DGA, also referred to as GGA).

In any of the methods of the present invention, in certain embodiments, the LFA-1 antagonist is an anti-LFA-antibody or an anti-ICAM 1 antibody. In one embodiment, the LFA-1 antagonist is an anti-CD11a antibody. In one embodiment, the anti-CD11a antibody is efalizumab.

In the present methods of alleviation, to minimize side effects, in particular infusion reactions on initial dosing, the patient can be administered the antagonist compound or antibody at an initial conditioning dose before the therapeutic dose, wherein the conditioning dose is lower than the therapeutic dose. Where the LFA-1 antagonist is efalizumab, the antibody can be administered at a dosage of between 0.3 mg/kg to 4 mg/kg. In one embodiment, the efalizumab antibody is administered at 1 mg/kg weekly. In another embodiment, efalizumab is administered at 2 mg/kg weekly. Where the LFA-1 antagonist used is efalizumab, in one embodiment, the patient is administered a conditioning dose of efalizumab at 0.7 mg/kg. In a further embodiment, the antibody is administered at an initial conditioning dose of 0.7 mg/kg during the first week followed by a dose of 1 mg/kg weekly for at least 4 weeks. In separate embodiments, the patient is administered the weekly therapeutic dose of 1 mg/kg or 2 mg/kg for 8 weeks, 11 weeks, or 24 weeks In any of the embodiments of the present methods of alleviating the disease, in a preferred embodiment, the LFA-1 antagonist is administered subcutaneously. In another embodiment the LFA-1 antagonist is administered intravenously.

In any of the embodiments of the method of alleviating granuloma annulare and sarcoid, the LFA-1 antagonist can be administered in conjunction with another therapy, a second therapeutic agent or an immunosuppressive agent. The second therapeutic agent is selected from the group consisting of cyclosporine, isotretinoin, etretinate, topical and systemic corticosteroids, fumaric acid esters, psoralens plus ultraviolet A (PUVA), potassium iodide, pentoxifylline, topical vitamin E, hydroxychloroquine, dapsone, niacinamide, low-dose chlorambucil, clofazimine, and a 5-lipoxygenase inhibitor plus vitamin E. In one embodiment, the second therapeutic agent is clofazimine or cyclosporine. Another second therapeutic agent is an immunoadhesin, in particular, Enbrel® or Amevive®.

The second therapeutic agent and the LFA-1 antagonist can be administered consecutively, sequentially, or a combination of both, in either order.

Yet another aspect of the method of the invention is to alleviate granuloma annulare or sarcoid in a patient suffering from a relapse of the disease or a patient who is non-responsive to other therapy used to treat the disease.

In one embodiment, patient having the disease is experiencing an inadequate response or is non-responsive to cyclosporine or clofazimine treatment.

Also provided by the invention is an article of manufacture comprising a container containing an efalizumab composition, and a package insert indicating that the composition can be used to treat disseminated granuloma annulare.

BRIEF DESCRIPTION OF THE FIGURES

FIG. 1B is a close-up of FIG. 1A.

DETAILED DESCRIPTION OF THE PREFERRED EMBODIMENTS

Figure 1B:
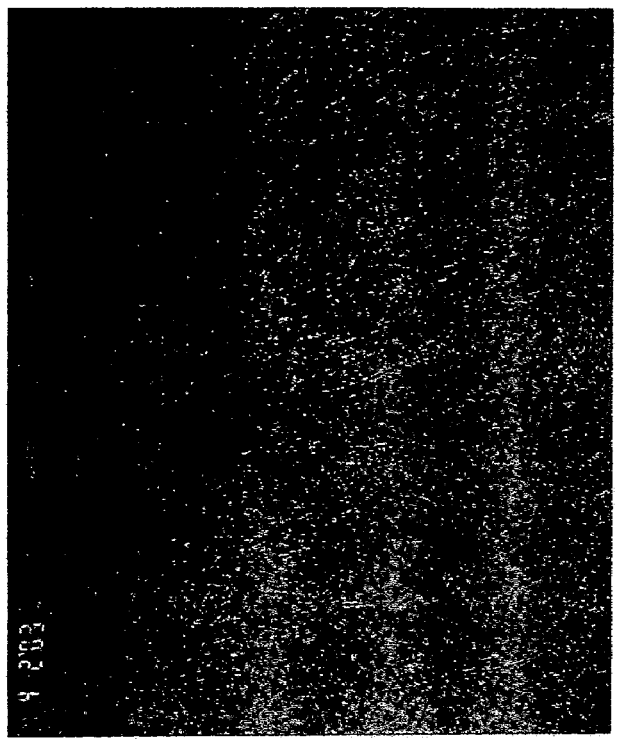
FIGS. 1A and 1B are photographs of the dorsum of the patient's right hand, a spot previously affected by DGA showing excellent clearance and are representative of the patient's overall response to treatment with the anti-CD11a antibody.

Granuloma annulare encompasses an uncommon benign group of granulomatous diseases that include localized, disseminated (generalized), subcutaneous, and perforating types. Approximately 10% to 15% of patients have disseminated granuloma annulare (DGA), which occurs primarily in adults and is characterized by multiple discrete or confluent papules with either an annular or nonannular configuration. DGA occurs predominantly on the trunk and proximal extremities, and patients with DGA may present with hundreds of lesions. In approximately one third of cases, patients report symptoms of pruritus or burning sensations. Histologically, DGA typically is characterized by areas of collagen alteration and elastic fiber degeneration in the middle and upper dermis surrounded by palisading inflammatory cells; the epidermis appears normal. The inflammatory infiltrates in DGA are primarily composed of a mixture of histiocytes (macrophages) and lymphocytes.

"Alleviating" in the context of the methods of the invention refers to therapeutic treatment wherein the object is to lessen the pathologic condition or disorder. A subject is successfully "alleviated" of a granuloma annulare disease if, after receiving a therapeutic amount of an LFA-1 antagonist of the invention according to the methods of the present invention, the subject shows observable and/or measurable reduction in or absence of one or more signs or symptoms of the disease as compared to baseline levels before receiving the treatment. The measurable signs or symptoms are for instance the size and number of skin lesions. Reduction of one or more symptoms of the disease may also be felt by the patient. Alleviation can achieve a complete response or resolution, defined as disappearance of all signs or symptoms, or a partial response. If the patient is not completely devoid of measurable signs and symptoms after receiving treatment, preferably the patient shows improvement in signs, symptoms of the disease by at least 20%, more preferably at least 40%, even more preferably at least 50%, more preferably by 70% or 75%, most preferably by 90% or greater, such as 95%, as compared to baseline measurements. These parameters for assessing successful treatment and improvement in the disease are readily measurable by routine procedures familiar to a physician of appropriate skill in the art.

"Chronic" administration refers to administration of the agent(s) in a continuous mode as opposed to an acute mode, so as to maintain the initial therapeutic effect (activity) for an extended period of time. "Intermittent" administration is treatment that is done not consecutively without interruption, but rather is cyclic in nature.

A "conditioning dose" is a dose which attenuates or reduces the frequency or the severity of first dose adverse side effects associated with administration of a therapeutic compound. The conditioning dose may be a therapeutic dose, a sub-therapeutic dose. A therapeutic dose is a dose which exhibits a therapeutic effect on the patient and a sub-therapeutic dose is a dose which dose not exhibit a therapeutic effect on the patient treated.

A "therapeutically effective amount" refers to the minimum concentrations (amount) of an LFA-1 antagonist administered to a mammal that are effective in at least attenuating a pathological symptom (e.g. causing, inducing or resulting in a detectable/measurable improvement; lessen the severity, extent or duration of symptoms) which occurs as a result of the granuloma annulare disorder. The symptoms may vary with the types of granuloma annulare; however, the symptoms of a particular granuloma annulare disorder and the means of detecting or measuring improvement in the symptoms e.g., in the size and number of the skin lesions, will be familiar to the physician of skill in the art.

LFA-1 (leukocyte function associated antigen) is an integrin receptor involved in cell adherence interactions. LFA-1 consists of the a subunit CD11a and the β subunit CD18. LFA-1 is expressed on all leukocytes.

The term "LFA-1 antagonist" generally refers to an antibody directed against either CD11a or CD18 or both, but also includes ICAM-1, soluble forms of ICAM-1 (e.g., the ICAM-1 extracellular domain, alone or fused to an immunoglobulin sequence), antibodies to ICAM-1, and fragments thereof, or other molecules capable of inhibiting the interaction of LFA-1 and ICAM-1.

Suitable LFA-1 antagonists include any compound which inhibits the interaction of LFA-1 and a receptor therefor, in particular, ICAM-1. The LFA-1 antagonist may be a small molecule, peptide, protein, immunoadhesin, an anti-LFA-1 antibody, or a fragment thereof, for example. These terms refer to antagonists directed against either CD11a or CD18 or both. Preferably, the antagonist is directed to or binds to the CD11a subunit or LFA-1 as a unit. Anti-CD11a antibodies include, e.g., MHM24 [Hildreth et al., *Eur. J. Immunol.*, 13: 202-208 (1983)], R3.1 (IgG1) [R. Rothlein, Boehringer Ingelheim Pharmaceuticals, Inc., Ridgefield, Conn.], 25-3 (or 25.3), an IgG1 available from Immunotech, France [Olive et al., in Feldmann, ed., *Human T cell Clones. A new Approach to Immune Regulation*, Clifton, N.J., Humana, 1986 p. 173], KBA (IgG2a) [Nishimura et al., *Cell. Immunol.*, 107: 32 (1987); Nishimura et al., ibid., 94: 122 (1985)], M7/15 (IgG2b) [Springer et al., *Immunol. Rev.*, 68: 171 (1982)], IOT16 [Vermot Desroches et al., *Scand. J. Immunol.*, 33: 277-286 (1991)], SPVL7 [Vermot Desroches et al., supra], and M17 (IgG2a) also referred to as M17/4, available from ATCC, (hybridoma Accession no. TIB-217) which are rat anti-murine CD11a antibodies. A preferred anti-CD11a antibody is a humanized antibody, efalizumab (Raptiva™; Genentech, Calif.). Other preferred anti-CD11a antibodies are the humanized antibodies described in U.S. Pat. No. 6,037,454. It is also generally preferred that the anti-CD11a antibodies are not T-cell depleting antibodies, that is, that the administration of the anti-CD11a antibody does not reduce the level of circulating T-cells.

In one embodiment, the humanized anti-CD11a antibody is one that comprises the

```
VL sequence of                              (SEQ ID NO. 1)
DIQMTQSPSSLSASVGDRVTITCRASKTISKYLAWYQQKPGKAPKLLIYS
GSTLQSGVPSRFSGSGSGTDFTLTISSLQPEDFATYYCQQHNEYPLTFGQ
GTKVEIK,
and VH sequence of                              (SEQ ID NO. 2)
EVQLVESGGGLVQPGGSLRLSCAASGYSFTGHWMNWVRQAPGKGLEWVGM
IHPSDSETRYNQKFKDRFTISVDKSKNTLYLQMNSLRAEDTAVYYCARGI
YFYGTFFYFDYWGQGTLVTVSS;
or
```

In another embodiment, the anti-CD11a antibody is one that comprises the MHM24 VL sequence

```
                                            (SEQ ID NO. 3)
DVQITQSPSYLAASPGETISINCRASKTISKYLAWYQEKPGKTNKLLIYS
GSTLQSGIPSRFSGSGSGTDFTLTISSLEPEDFAMYYCQQHNEYPLTFGT
GTKLELK,
and MHM24 VH sequence                           (SEQ ID NO. 4)
EVQLQQPGAELMRPGASVKLSCKASGYSFTGHWMNWVRQRPGQGLEWIGM
IHPSDSETRLNQKFKDKATLTVDKSSSSAYMQLSSPTSEDSAVYYCARGI
YFYGTTYFDYWGQGTTLTVSS.
```

Examples of anti-CD18 antibodies include MHM23 [Hildreth et al., supra], M18/2 (IgG2a) [Sanches-Madrid et al., *J. Exp. Med.*, 158: 586 (1983)], H52 [Fekete et al., *J. Clin. Lab Immunol.*, 31: 145-149 (1990)], Mas191c [Vermot Desroches et al., supra], IOT18 [Vermot Desroches et al., supra], 60.3 [Taylor et al., *Clin. Exp. Immunol.*, 71: 324-328 (1988)], and 60.1 [Campana et al., *Eur. J. Immunol.*, 16: 537-542 (1986)]. See also U.S. Pat. No. 5,997,867.

Other examples of suitable LFA-1 binding molecules, including antibodies, are described in Hutchings et al., supra, WO 98/51343, WO 91/18011, WO 91/16928, WO 91/16927, Can. Pat. Appln. 2,008,368, WO 90/15076, WO 90/10652, WO 90/13281, WO 93/06864, WO 93/21953, EP 387,668, EP 379,904, EP 346,078, U.S. Pat. No. 5,932,448, U.S. Pat. No. 5,622,700, U.S. Pat. No. 5,597,567, U.S. Pat. No. 5,071,964, U.S. Pat. No. 5,002,869, U.S. Pat. No. 5,730,983, Australian Pat. Appln. 8815518, FR 2700471A, EP 289,949, EP 362526, and EP 303,692.

A "small molecule" is defined herein to have a molecular weight below about 600 daltons, and is generally an organic compound.

"Efalizumab" (Raptiva®) is a recombinant humanized IgG1 kappa isotype monoclonal antibody that binds to human CD11a (U.S. Pat. No. 6,037,454). Commercially available from Genentech, Inc., Raptiva is an FDA approved drug for psoriasis treatment. Efalizumab binds with high specificity and affinity to CD11a, the a subunit of leukocyte function-associated antigen 1 (LFA-1) on the surface of T cells, preventing LFA-1 from binding with one of its ligands, intercellular adhesion molecule-1 (ICAM-1), and inhibiting multiple T-cell interactions. Interaction between LFA-1 and ICAM-1 contributes to the initiation and maintenance of multiple processes, including activation of T-lymphocytes, adhesion of T-lymphocytes to endothelial cells, and migration of T-lymphocytes to sites of inflammation including psoriatic and granulomatous skin.

RAPTIVA® (efalizumab) is supplied as a sterile, lyophilized powder in single-use glass vials for subcutaneous (SC) injection. Reconstitution of the single-use vial with 1.3 mL of the supplied sterile water for injection yields 100 mg/mL of RAPTIVA. Each single-use vial of RAPTIVA contains 150 mg of efalizumab, 123.2 mg of sucrose, 6.8 mg of L-histidine hydrochloride monohydrate, 4.3 mg of L-histidine and 3 mg of polysorbate 20 and is designed to deliver 125 mg of efalizumab in 1.25 mL.

"ENBREL" (etanercept; Amgen, Calif.) is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. Etanercept binds specifically to tumor necrosis factor (TNF) and blocks its interaction with cell surface TNF receptors. It inhibits the activity of TNF.

The term "antibody" is used in the broadest sense and specifically covers monoclonal antibodies (including full length monoclonal antibodies), multispecific antibodies (e.g., bispecific antibodies), and antibody fragments so long as they exhibit the desired biological activity or function.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

"Functional fragments" of the antagonist antibodies of the invention are those fragments that retain binding to LFA-1, CD11a, or their ligand with substantially the same affinity as the intact full length molecule from which they are derived and show biological activity.

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl.*

*Acad. Sci. USA* 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Compositions and Methods of the Invention

According to one embodiment, the LFA-1 antagonist is an immunoadhesin, e.g., Amevive® (Biogen, Boston, Mass.)

In the methods of treatment of the present invention, the LFA-1 antagonist can be administered chronically or intermittently.

The patient can be treated with the LFA-1 antagonists in conjunction with one or more therapeutic agents. Second therapeutic agents useful in the treatment of granuloma annulare include the following: cyclosporine, isotretinoin, etretinate, topical and systemic corticosteroids, fumaric acid esters, psoralens plus ultraviolet A (PUVA), potassium iodide, pentoxifylline, topical vitamin E, hydroxychloroquine, dapsone, niacinamide, low-dose chlorambucil, clofazimine, and a 5-lipoxygenase inhibitor plus vitamin E.

"Immunosuppressive agent" as used herein refers to substances that act to suppress or mask the immune system of a patient. Such agents would include substances that suppress cytokine production, down regulate or suppress self-antigen expression, or mask the MHC antigens. Examples of such agents include steroids such as glucocorticosteroids, e.g., prednisone, methylprednisolone, and dexamethasone; 2-amino-6-aryl-5-substituted pyrimidines (see U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; cytokine or cytokine receptor antagonists including anti-interferon-$\gamma$, -$\beta$, or -$\alpha$ antibodies; anti-tumor necrosis factor-$\alpha$ antibodies; anti-tumor necrosis factor-$\beta$ antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-$\beta$; streptodomase; RNA or DNA from the host; FK506; RS-61443; deoxyspergualin; rapamycin; T-cell receptor (U.S. Pat. No. 5,114,721); T-cell receptor fragments (Offner et al., *Science* 251:430-432 (1991); WO 90/11294; and WO 91/01133); and T cell receptor antibodies (EP 340,109) such as T10B9. The immunosuppressive agents herein may overlap with the second therapeutic agent.

Dosing

For the methods of the invention, the antagonists and antibodies of the invention will be administered at a dosage that is efficacious for the treatment of the granuloma annulare or sarcoid disease while minimizing toxicity and side effects.

The LFA-1 antibodies can be administered to the patient in a dosage range of about 1 mg/kg to 20 mg/kg. In different embodiments, the dosage range is 1-15 mg/kg, 1-10 mg/kg, 2-10 mg/kg, 3-10 mg/kg. Efalizumab antibody can be administered at a dosage range of from 0.3 mg/kg to 4 mg/kg, at least once a week for at least 4 weeks.

Doses of efalizumab of up to 4 mg/kg/wk SC for 10 weeks following a conditioning (0.7 mg/kg) first dose have been administered without an observed increase in acute toxicity.

In one embodiment, efalizumab is administered to the patient subcutaneously as an initial conditioning dose of 0.7 mg/kg followed by 11 weekly SC (subcutaneous) doses of 1 mg/kg/wk. The initial lower conditioning dose is optional; the patient can receive instead 12 weekly doses at 1 mg/kg/wk.

In treating disease, the LFA-1 antagonists of the invention can be administered to the patient chronically or intermittently, as determined by the physician of skill in the disease.

A patient administered a drug by intravenous infusion or subcutaneously may experience adverse events such as fever, chills, burning sensation, asthenia and headache. To alleviate or minimize such adverse events, the patient may receive an initial conditioning dose(s) of the antibody followed by a therapeutic dose. The conditioning dose(s) will be lower than the therapeutic dose to condition the patient to tolerate higher dosages.

"Initial" dosing means dosing that is not the last dosing administered in the treatment. The initial dosing need not be a single dose, but it is not the last dose. "Subsequent" dosing is dosing that follows the initial dosing and includes the last dose administered for the treatment.

Route of Administration

The antagonists and antibodies as well as second therapeutic agents and immunosuppressive agents used in the methods of the invention are administered to a human patient in accord with methods known to medical practitioners, such as by intravenous administration, e.g., as a bolus or by continuous infusion over a period of time, by subcutaneous, topically, intramuscular, intra-arterial, intrapulmonary, intra-articular, intrasynovial, intrathecal, intralesional, or inhalation routes (e.g., intranasal), generally by subcutaneous, intravenous or topical administration.

The LFA-1 antagonist, the second therapeutic agent and immunosuppressive agent can be provided systemically or topically. In one embodiment, the LFA-1 antagonist is administered topically.

Pharmaceutical Formulations

Therapeutic formulations of the antagonists and antibodies used in accordance with the present invention are prepared for storage by mixing the compound or antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The LFA-1 antagonists useful in the methods of the present invention can be provided in an extended release formulation.

The term "extended-release" or "sustained-release" formulations in the broadest possible sense means a formulation of an active LFA-1 antagonist compound resulting in the release or activation of the compound for a sustained or extended period of time or at least for a period of time which is longer than if the compound was made available in vivo in the native or unformulated state. Optionally, the extended-release formulation occurs at a constant rate and/or results in sustained and/or continuous concentration of the active polypeptide. Suitable extended release formulations may comprise microencapsulation, semi-permeable matrices of solid hydrophobic polymers, biogradable polymers, biodegradable hydrogels, suspensions or emulsions (e.g., oil-in-water or water-in-oil). Optionally, the extended-release formulation comprises poly-lactic-co-glycolic acid (PLGA) and can be prepared as described in Lewis, "Controlled Release of Bioactive Agents form Lactide/Glycolide polymer," in Biodegradable Polymers as Drug Delivery Systems, M. Chasin & R. Langeer, Ed. (Marcel Dekker, New York), pp. 1-41. Optionally, the extended-release formulation is stable and the activity of the LFA-1 antagonist does not appreciably diminish with storage over time. More specifically, such stability can be enhanced through the presence of a stabilizing agent such as a water-soluble polyvalent metal salt.

Articles of Manufacture and Kits

Another embodiment of the invention is an article of manufacture containing materials useful for the treatment of granuloma annulare or sarcoid disease. The article of manufacture comprises at least one container and a label or package insert on or associated with the container. Suitable containers include, for example, bottles, vials, syringes, etc. The containers may be formed from a variety of materials such as glass or plastic. At least one container holds a composition which is effective for treating the condition and may have a sterile access port (for example the container may be an intravenous solution bag or a vial having a stopper pierceable by a hypodermic injection needle). Two therapeutic compositions may be provided in the article of manufacture. At least one active agent in the first composition is a CD11a binding antibody of the invention. The second or second and third compositions may be held in one or more separate containers. The label or package insert indicates that the composition is used for treating granuloma annulare, DGA or sarcoid. The label or package insert will further comprise instructions for administering the compositions to the patient. Package insert refers to instructions customarily included in commercial packages of therapeutic products, that contain information about the indications, usage, dosage, administration, contraindications and/or warnings concerning the use of such therapeutic products. Additionally, the article of manufacture may further comprise a container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In a specific embodiment, the container contains an efalizumab composition, and the package insert indicates that the composition can be used to treat disseminated granuloma annulare (DGA).

Experimental Examples

This report describes a case of a patient with moderate to severe psoriasis with severe DGA that resolved upon treatment with efalizumab (anti-CD11a), a novel biologic T-cell modulator.

A 52-year old male with a history of moderate to severe plaque psoriasis was first diagnosed with granuloma annulare in 1999, with lesions initially appearing on his hands. A review of his medical history revealed that he did not have diabetes mellitus, a disease state with questionable association with granuloma annulare. Within months of his initial diagnosis, the lesions spread to his arms, shoulders, and neck.

In December 1999, the DGA lesions were biopsied, confirming the diagnosis of DGA. From March 2000 through October 2002, this patient was treated with numerous agents in an attempt to manage his plaque psoriasis and DGA, including systemic therapies such as cyclosporine and clofazimine; intralesional corticosteroids; psoralen plus ultraviolet A (PUVA); and topical therapies such as corticosteroids, desoximetasone, tazarotene, clobetasol propionate, and tacrolimus ointment, all with varying levels of efficacy. Control of this patient's plaque psoriasis and DGA were further complicated by the development of renal dysfunction related to cyclosporine and intolerance secondary to clofazimine-induced diarrhea.

Figure 1A:

In October 2002, this patient was enrolled into an efalizumab Phase III clinical trial for patients with moderate to severe plaque psoriasis. All psoriasis therapies were discontinued as he entered the 4-week washout phase prior to administration of study drug. In November 2002, the patient began efalizumab therapy (anti-CD11a monoclonal antibody) at a dose of 1 mg/kg weekly, for 12 weeks, by subcutaneous injection. The baseline Psoriasis Area and Severity Index (PASI) was 12.6. The planned duration of study therapy was 12 weeks followed by extended open-label treatment for up to an additional 48 weeks of continuous therapy at a dose of 1 mg/kg/wk. Following initiation of efalizumab therapy, the patient's DGA cleared rapidly, with marked improvement noted within 4 weeks of initiating efalizumab therapy. By January, the DGA was resolved (see FIG. 1). In April 2003, the clofazimine was discontinued. As of July 2003, the DGA remains in remission, with the exception of post-inflammatory pigmentation, and the patient's PASI scores remained markedly improved and at the level achieved at Week 12, demonstrating maintenance of the improvement achieved at the completion of efalizumab therapy.

Within 2 months after receiving efalizumab, the patient's DGA had resolved. This is the first case report of rapid and successful treatment of severe DGA with an exemplary LFA-1 antagonist, efalizumab.

REFERENCES

References cited within this application, including patents, published applications and other publications, are hereby incorporated by reference.

1. Friedman-Birnbaum R. Generalized and localized granuloma annulare. *Int J Dermatol.* 1986; 25:364-366.
2. Dabski K, Winkelmann R K. Generalized granuloma annulare: clinical and laboratory findings in 100 patients. *J Am Acad Dermatol.* 1989; 20:39-47.
3. Muhlbauer J E. Granuloma annulare. *J Am Acad Dermatol.* 1980; 3:217-230.
4. Dabski K, Winkelmann R K. Generalized granuloma annulare: histopathology and immunopathology. Systematic review of 100 cases and comparison with localized granuloma annulare. *J Am Acad Dermatol.* 1989; 20:28-39.
5. Friedman-Birnbaum R, Weltfriend S, Kerner H, Lichtig C. Elastic tissue changes in generalized granuloma annulare. *Am J Dermatopathol.* 1989; 11:429-433.
6. Hanna W M, Moreno-Merlo F, Andrighetti L. Granuloma annulare: an elastic tissue disease? Case report and literature review. *Ultrastruct Pathol.* 1999; 23:33-38.
7. Smith M D, Downie J B, DiCostanzo D. Granuloma annulare. Int *J Dermatol.* 1997; 36:326-333.
8. Buechner S A, Winkelmann R K, Banks P M. Identification of T-cell subpopulations in granuloma annulare. *Arch Dermatol.* 1983; 119:125-128.
9. Modlin R L, Vaccaro S A, Gottlieb B, Gebhard J F, Linden C E, Forni M et al. Granuloma annulare. Identification of cells in the cutaneous infiltrate by immunoperoxidase techniques. *Arch Pathol Lab Med.* 1984; 108:379-382.
10. Modlin R L, Horwitz D A, Jordan R R, Gebhard J F, Taylor C R, Rea T H. Immunopathologic demonstration of T lymphocyte subpopulations and interleukin 2 in granuloma annulare. *Pediatr Dermatol.* 1984; 2:26-32.
11. Fayyazi A, Schweyer S, Eichmeyer B, Herms J, Hemmerlein B, Radzun H J et al. Expression of IFN□, coexpression of TNF□ and matrix metalloproteinases and apoptosis of T lymphocytes and macrophages in granuloma annulare. *Arch Dermatol Res.* 2000; 292:384-390.
12. Delves P J, Roitt I M. The immune system. Second of two parts. *N Engl J Med.* 2000; 343:108-117.
13. Ahmed A A, Nordlind K, Schultzberg M, Liden S. Interleukin-1 alpha- and beta-, interleukin-6- and tumour necrosis factor-alpha-like immunoreactivities in chronic granulomatous skin conditions. *Acta Derm Venereol.* 1994; 74:435-440.
14. Mempel M, Musette P, Flageul B, Schnopp C, Remling R, Gachelin G et al. T-cell receptor repertoire and cytokine pattern in granuloma annulare: defining a particular type of cutaneous granulomatous inflammation. *J Invest Dermatol.* 2002; 118:957-966.
15. Barron D F, Cootauco M H, Cohen B A. Granuloma annulare. A clinical review. *Lippincotts Prim Care Pract.* 1997; 1:33-39.
16. Filotico R, Vena G A, Coviello C, Angelini G. Cyclosporine in the treatment of generalized granuloma annulare. *J Am Acad Dermatol.* 1994; 30:487-488.
17. Ho V C. Cyclosporine in the treatment of generalized granuloma annulare. *J Am Acad Dermatol.* 1995; 32(2 Pt 1):298.
18. Schleicher S M, Milstein H J, Lim S J, Stanton C D. Resolution of disseminated granuloma annulare with isotretinoin. *Int J Dermatol.* 1992; 31:371-372.
19. Tang W Y M, Chong L Y, Lo K K. Resolution of generalized granuloma annulare with isotretinoin therapy. *Int J Dermatol.* 1996; 35:455-456.
20. Adams D C. Improvement of chronic generalized granuloma annulare with isotretinoin. *Arch Dermatol.* 2002; 138:1518-1519.
21. Botella-Estrada R, Guillen C, Sanmartin O, Aliaga A. Disseminated granuloma annulare: resolution with etretinate therapy. *J Am Acad Dermatol.* 1992; 26:777-778.
22. Takigawa M, Aoshima T. Generalized granuloma anulare in a 15-month-old infant. *Dermatologica.* 1976; 153:202-206.
23. Volden G. Successful treatment of chronic skin diseases with clobetasol propionate and a hydrocolloid occlusive dressing. *Acta Derm Venereol.* 1992; 72:69-71.
24. Kreuter A, Gambichler T, Altmeyer P, Brockmeyer N H. Treatment of disseminated granuloma annulare with fumaric acid esters. *BMC Dermatol.* 2002; 2:5.
25. Kerker B J, Huang C P, Morison W L. Photochemotherapy of generalized granuloma annulare. *Arch Dermatol.* 1990; 126:359-361.
26. Setterfield J, Huilgol S C, Black M M. Generalised granuloma annulare successfully treated with PUVA. *Clin Exp Dermatol.* 1999; 24:458-460.
27. Giessel M, Graves K, Kalivas J. Treatment of disseminated granuloma annulare with potassium iodide. *Arch Dermatol.* 1979; 115:639-640.
28. Smith J B, Hansen C D, Zone J J. Potassium iodide in the treatment of disseminated granuloma annulare. *J Am Acad Dermatol.* 1994; 30:791-792.
29. Rubel D M, Wood G, Rosen R, Jopp-McKay A. Generalised granuloma annulare successfully treated with pentoxifylline. *Australas J Dermatol.* 1993; 34:103-108.
30. Burg G. Disseminated granuloma anulare: therapy with vitamin E topically. *Dermatology.* 1992; 184:308-309.
31. Carlin M C, Ratz J L. A case of generalized granuloma annulare responding to hydroxychloroquine. *Cleve Clin J Med.* 1987; 54:229-232.
32. Saied N, Schwartz R A, Estes S A. Treatment of generalized granuloma annulare with dapsone. *Arch Dermatol.* 1980; 116:1345-1346.
33. Czarnecki D B, Gin D. The response of generalized granuloma annulare to dapsone. *Acta Derm Venereol.* 1986; 66:82-84.
34. Ma A, Medenica M. Response of generalized granuloma annulare to high-dose niacinamide. *Arch Dermatol.* 1983; 119:836-839.

35. Kossard S, Winkelmann R K. Low-dose chlorambucil in the treatment of generalized granuloma annulare. *Dermatologica* 1979; 158:443-450.
36. Rudolph R I. Disseminated granuloma annulare treated with low-dose chlorambucil. *Arch Dermatol.* 1979; 115: 1212-1213.
37. Antony F, Holden C A. Sweet's syndrome in association with generalized granuloma annulare in a patient with previous breast carcinoma. *Clin Exp Dermatol.* 2001; 26:668-670.
38. Smith K J, Norwood C, Skelton H. Treatment of disseminated granuloma annulare with a 5-lipoxygenase inhibitor and vitamin E. *Br J Dermatol.* 2002; 146:667-670.
39. Werther W A, Gonzalez T N, O'Connor S J, McCabe S, Chan B, Hotaling T et al. Humanization of an anti-lymphocyte function-associated antigen (LFA)-1 monoclonal antibody and reengineering of the humanized antibody for binding to rhesus LFA-1. *J Immunol.* 1996; 157:4986-4995.

What is claimed is:

1. A method of alleviating a disseminated granuloma annulare comprising administering to a patient having the disease, a therapeutically effective amount of an LFA-1 antagonist wherein the LFA-1 antagonists is an anti-CD11a antibody.

2. The method of claim 1, wherein the anti-CD11a antibody is efalizumab.

3. The method of claim 2, wherein the antibody is administered at between 0.3 mg/kg to 4 mg/kg.

4. The method of claim 3, wherein the antibody is administered at 1 mg/kg weekly.

5. The method of claim 3, wherein the antibody is administered at 2 mg/kg weekly.

6. The method of claim 3 or claim 4, wherein the patient is administered the antibody at an initial conditioning dose before the therapeutic dose.

7. The method of claim 6, wherein the conditioning dose is 0.7 mg/kg.

8. The method of claim 2, wherein the antibody is administered at an initial conditioning dose of 0.7 mg/kg during the first week followed by a dose of 1 mg/kg weekly for at least 4 weeks.

9. The method of claim 8, wherein the dose of 1 mg/kg is administered for at least 11 weeks.

10. The method of claim 1, wherein the LFA-1 antagonist is administered subcutaneously.

11. The method of any one of claims 4, 5, and 9, wherein the LFA-1 antagonist is administered subcutaneously.

12. The method of claim 1 wherein the LFA-1 antagonist is administered intravenously.

13. The method of claim 1 or 2 wherein the LFA-1 antagonist is administered in conjunction with a second therapeutic agent or an immunosuppressive agent.

14. The method of claim 13, wherein the second therapeutic agent is selected from the group consisting of cyclosporine, isotretinoin, etretinate, topical and systemic corticosteroids, fumaric acid esters, psoralens plus ultraviolet A (PUVA), potassium iodide, pentoxifylline, topical vitamin E, hydroxychloroquine, dapsone, niacinamide, low-dose chlorambucil, clofazimine, and a 5-lipoxygenase inhibitor plus vitamin E.

15. The method of 14, wherein the second therapeutic agent is clofazimine or cyclosporine.

16. The method of claim 14, wherein the second therapeutic agent and the LFA-1 antagonist are administered concurrently.

17. The method of claim 14, wherein the second therapeutic agent and the LFA-1 antagonist are administered sequentially in either order.

18. The method of claim 14, wherein the second therapeutic agent and the LFA-1 antagonist are administered in a combination of concurrently and sequentially in either order.

19. The method of claim 1 wherein the patient is non-responsive to other therapy.

20. The method of claim 1 wherein the granuloma annulare is resolved within 2 months of initiation of therapy with the LFA-1 antagonist.

* * * * *